United States Patent [19]
Murphey et al.

[11] Patent Number: 5,533,996
[45] Date of Patent: Jul. 9, 1996

[54] TRANSFER SET CONNECTOR WITH PERMANENT, INTEGRAL CAM OPENING CLOSURE AND A METHOD OF USING THE SAME

[75] Inventors: Randy Murphey, Kenosha, Wis.; Marc Bellotti, Libertyville, Ill.; Ying-Cheng Lo, Green Oaks, Ill.; Scott Edwards, Liberyville, Ill.

[73] Assignee: Baxter International, Inc., Deerfield, Ill.

[21] Appl. No.: 295,112

[22] Filed: Aug. 24, 1994

[51] Int. Cl.⁶ .................................................. A61M 5/14
[52] U.S. Cl. ................................................. 604/283; 604/905
[58] Field of Search ........................ 604/905, 240–243, 604/411, 412, 413, 414, 283; 285/24–29, 178, 314

[56] References Cited

U.S. PATENT DOCUMENTS

| | | | |
|---|---|---|---|
| 4,306,705 | 12/1981 | Svensson | 604/905 |
| 4,338,933 | 7/1982 | Bayard et al. | 604/905 |
| 4,660,803 | 4/1987 | Johnston et al. | 285/24 |
| 4,846,506 | 7/1989 | Bocson et al. | 285/27 |
| 4,958,858 | 9/1990 | guest | 285/24 |

*Primary Examiner*—Randall L. Green
*Assistant Examiner*—Manuel Mendez
*Attorney, Agent, or Firm*—Thomas S. Borecki; Charles R. Mattenson; Robert M. Barrett

[57] ABSTRACT

A connector assembly is provided having a male component (12) and a female component (10) to provide fluid communication between a fluid source and a destination such as a patient. The female component (10) includes a door (28) rotatable about a hinge (30). The door (28) is forced open by a longitudinal member (34) within the male component (12). The door (28) is converted into a position parallel to the length of the female component (10) providing fluid communication between a tubing (36) extending into the female component (10). A sleeve (44) is further provided to permit and to prevent fluid flow through a tubing by rotation of the sleeve (44) resulting in compression and expansion of longitudinal members (46) within the sleeve (44) and thereby the tubing.

20 Claims, 3 Drawing Sheets

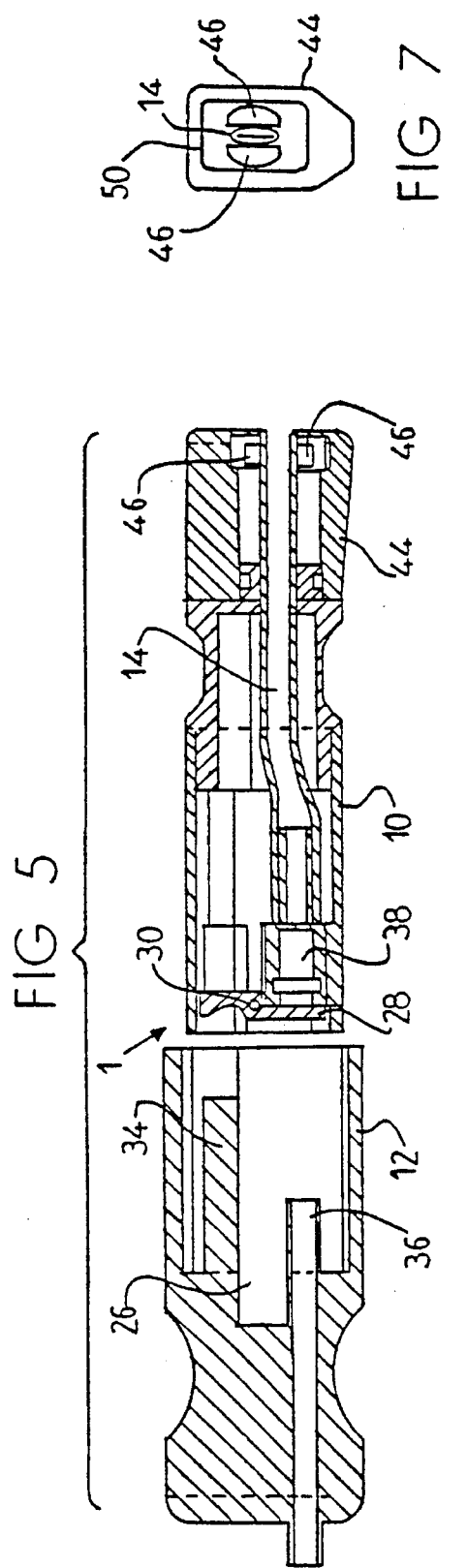
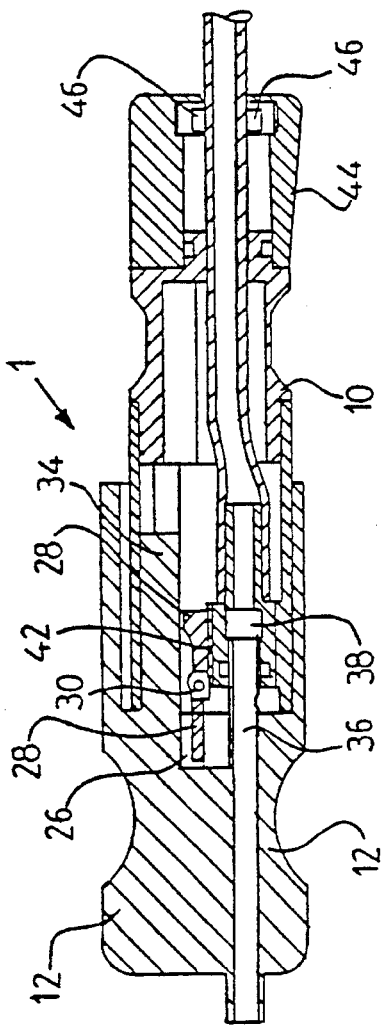

5,533,996

TRANSFER SET CONNECTOR WITH PERMANENT, INTEGRAL CAM OPENING CLOSURE AND A METHOD OF USING THE SAME

BACKGROUND OF THE INVENTION

The present invention generally relates to a connector assembly connecting a first length of tubing to a second length of tubing. More specifically, the present invention relates to a connector assembly having a hinged closure integrally formed with one component of the connector assembly.

In a variety of industries, and for a variety of applications, it is necessary to create and provide a flow path. In many situations, most specifically in the medical industry, it is necessary to create sterile fluid flow paths.

It is, of course, generally known to provide fluid delivery to a patient for a variety of purposes, such as delivery of a medicament, provide nutrition, and peritoneal dialysis and the like. Such fluid delivery necessitates in many instances the creation of sterile flow paths. Some such procedures require the sterile flow paths to be disconnected and reconnected.

For example, it is known to use a cannula or a needle to inject into a patient: a solution through the use of a length of tubing which is further connected to a container housing the solution. Often, an adaptor or other connector is provided for enabling fluid communication between the container and the patient through the tubing. For example, a connector may be provided at a port on the container to connect an end of the length of tubing to the container.

It is also well known to provide solutions to a patient, such as for peritoneal dialysis. In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. The proper acid-base electrolyte and fluid balance to be returned to the blood is achieved, and the dialysis solution is simply drained from the body cavity through the catheter.

This procedure is generally repeated three or four times daily for such a patient. Therefore, repeated connections and disconnections are required to be made from the system. Further, such a patient is often interrupted during administration of solution into the body requiring disconnection from the system.

At least three issues arise with respect to the disconnection and reconnection of a sterile flow path, such as that used for peritoneal dialysis. One requirement is that the system must provide a quick and a simple disconnection from the system. It is also required that a sterile, contaminant-free environment be maintained after disconnection. Further, the system must provide means for a simple reconnection to the system.

If dismantling of the entire setup is required, a patient generally will not permit the interruption and will continue receiving the solution ignoring the interruption. On the other hand, if the disconnection and/or reconnection cannot be performed without contaminating the system, the contaminated system components or the entire system must be replaced. In the alternative, the contaminated components of the system must be sterilized before reuse of the system. Again, therefore, the patient will ignore the interruption and continue with the administration of solution from the system.

At times, however, interruptions, such as emergencies, will require disconnection from the system. Therefore, a need exists for an improved system for simplifying disconnection and reconnection without contamination of the components of the system.

SUMMARY OF THE INVENTION

The present invention provides a connector assembly and a method of connecting a pair of connectors to provide fluid communication between a first length of tubing and a second length of tubing. The connector assembly incorporates a hinged closure providing sealed connection and disconnection of the assembly upon connection of the connectors.

To this end, in an embodiment, the present invention provides a connector assembly comprising a male component connected to a first length of tubing and a female component connected to a second length of tubing. The female component selectively mates with the male component providing communication between the first length of tubing and the second length of tubing. The female component comprises a hinged closure providing selected access to an orifice of the female component.

In an embodiment, the hinged closure of the connector assembly includes a spring to maintain a seal of the hinged closure.

In an embodiment, the hinged closure of the connector assembly includes a snap detent to maintain a seal of the hinged closure.

In an embodiment, the connector assembly further comprises a longitudinal member within the male component wherein the longitudinal member is capable of opening the hinged closure of the female component.

In an embodiment, the connector assembly further comprises a tubular member within the male component, the tubular member extending such that, when the male component mates with the female component, the orifice of the female component is in fluid communication with the tubular member.

In an embodiment, the orifice of the female component includes an O-ring. In another embodiment, the orifice of the female component has a luer taper.

In another embodiment, the connector assembly further comprises a clamp at an end of the male component or the female component, the clamp selectively occluding flow through the tubing. The clamp may be rotatable about an axis defined along a length of the tubing.

In another embodiment of the present invention, a connector assembly for providing fluid communication between a first length of tubing and a second length of tubing is provided. The connector assembly comprises a first component having a hinged closure connected to the first length of tubing. A second component has means for opening the hinged closure and is connected to the second length of tubing wherein connection of the first component to the second component opens the hinged closure and provides fluid communication between the first length of tubing and the second length of tubing.

In an embodiment, the connector assembly further comprises occluder means selectively preventing and permitting flow through one of the first lengths of tubing. The occluder means may be rotatable about an axis defined by the length of tubing.

In an embodiment, a mass is integrally formed on an interior side of the hinged closure, the mass sealing an opening of the first component. In an embodiment, the mass is antimicrobially impregnated.

In an embodiment, the connector assembly further comprises a spring applying tension to the hinged closure.

In an embodiment, the first component and the second component are constructed and arranged to prevent misalignment.

In another embodiment of the present invention, a method provides fluid communication between a first length of tubing connected to a patient and a second length of tubing connected to a fluid source. The method comprises the steps of: providing a first connector; providing a closure integrally formed with the first connector; providing a second connector; providing a means for opening the closure integrally formed with the second connector; and connecting the first connector with the second connector providing fluid communication between the first length of tubing and the second length of tubing wherein the means for opening of the second connector forces the closure to open upon connection.

In an embodiment, the method further comprises the step of providing an occluder for selectively preventing fluid communication.

In an embodiment, the method further comprises the step of rotating an occluder about an axis defined by a length of the tubing for selectively preventing fluid communication.

It is, therefore, an advantage of the present invention to provide a system and a method for connecting and disconnecting an assembly providing fluid communication between a source and a patient.

Another advantage of the present invention is to provide a system and a method for repeated connection and disconnection of a connector providing fluid communication between a source and a patient.

Yet another advantage of the present invention is to provide a simple connector that may readily connect and disconnect a first length of tubing from a second length of tubing in a sealed manner.

A still further advantage of the present invention is to provide a system and a method for connecting and disconnecting a connector between two lengths of tubing which may be easily performed by either a patient or other administrator.

Moreover, an advantage of the present invention is to provide a system and a method for connecting and disconnecting a connector between two lengths of tubing requiring few steps.

Yet another advantage of the present invention is to provide a system and a method for connecting and disconnecting a connector without requiring a liquid antimicrobial.

And, another advantage of the present invention is to provide a compact, ergonomic system for connecting and disconnecting a connector between two lengths of tubing.

Additional features and advantages of the present invention are described in, and will be apparent from, the detailed description of the presently preferred embodiments and from the drawings.

BRIEF DESCRIPTION OF THE DRAWINGS

FIG. 5 illustrates a cross-sectional view of the connector assembly immediately prior to connection between its male component and is female component.

FIG. 6 illustrates a cross-sectional view of the connector assembly of the present invention with the male component and the female component connected.

FIG. 7 illustrates an end view of the sleeve portion of the female component of the present invention.

DETAILED DESCRIPTION OF THE PRESENTLY PREFERRED EMBODIMENTS

The present invention provides a connector between two lengths of tubing or other conduit for selectively connecting and disconnecting the lengths of tubing. When connected, fluid communication is provided between a fluid source and a patient. Fluid, however, may be occluded from flowing when connected using an occluder integrally formed with the connector.

Figure 1:
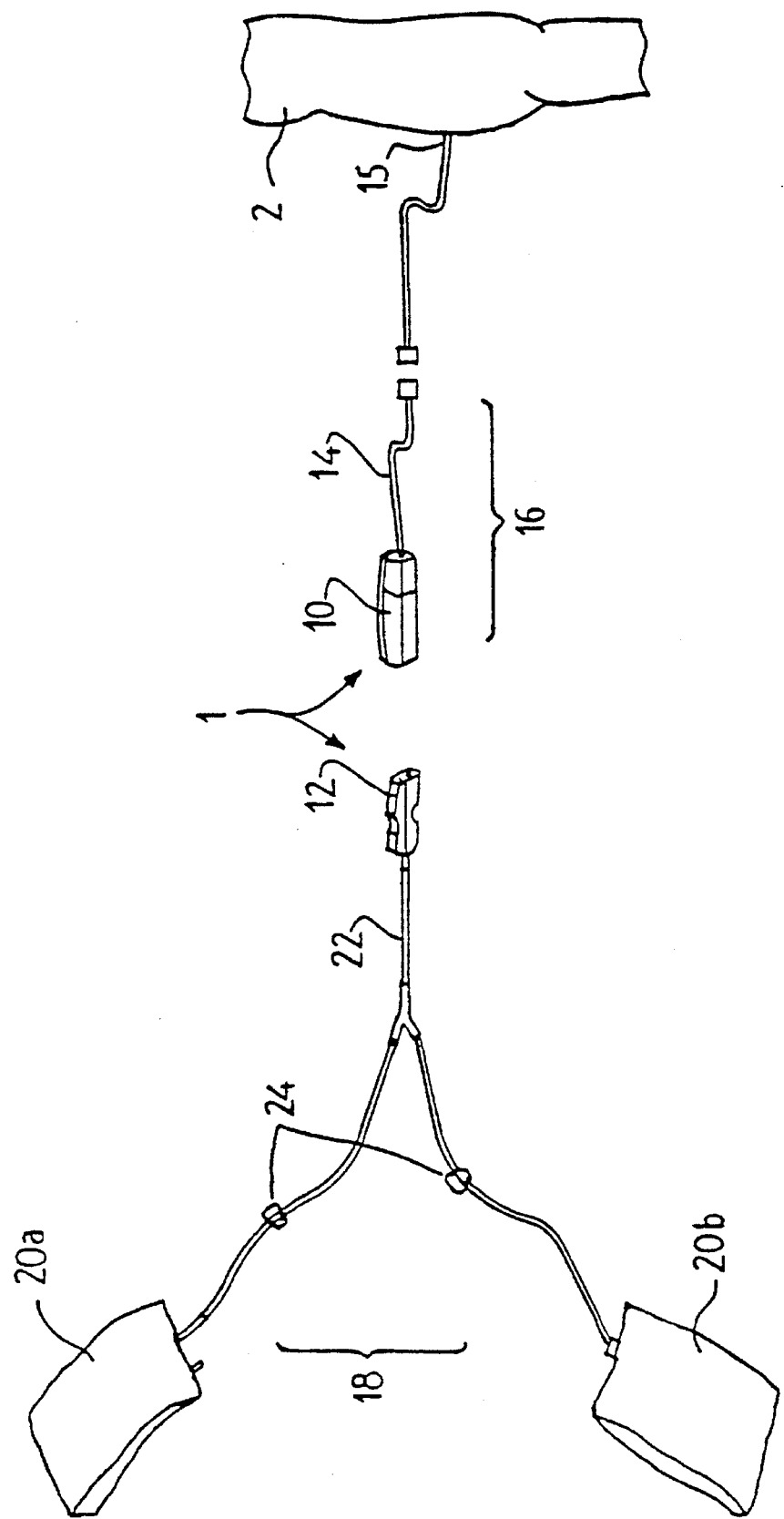
FIG. 1 illustrates an environmental view of a connector of the present invention in its disconnected state between a fluid source and a patient.

Referring now to the drawings, FIG. 1 illustrates an environmental view of a system employing the connector of the present invention. The connector is generally illustrated at 1 and includes a female component 10 and a male component 12. As illustrated in FIG. 1, in a preferred embodiment of the present invention, the female component 10 is connected to a conduit 14 which is attached via a catheter 15 to a patient 2.

The male component 12, on the other hand, in a preferred embodiment, may be connected to a Y-set generally illustrated at 18. The Y-set 18 includes two flexible containers 20a, 20b. Typically, for peritoneal dialysis, one of the flexible containers, for example, the flexible container 20a, is filled with a dialysate and the other flexible container 20b is empty. The flexible containers 20a and 20b are attached to the male component 12 through a length of conduit 22 forming a portion of the Y-set 18. Clamps 24 may be provided at any point along the length of the conduit 22 to control flow of dialysate as desired. In another embodiment, the male component 12 of the connector 1 may have clamps integrated into its housing.

Figure 4:
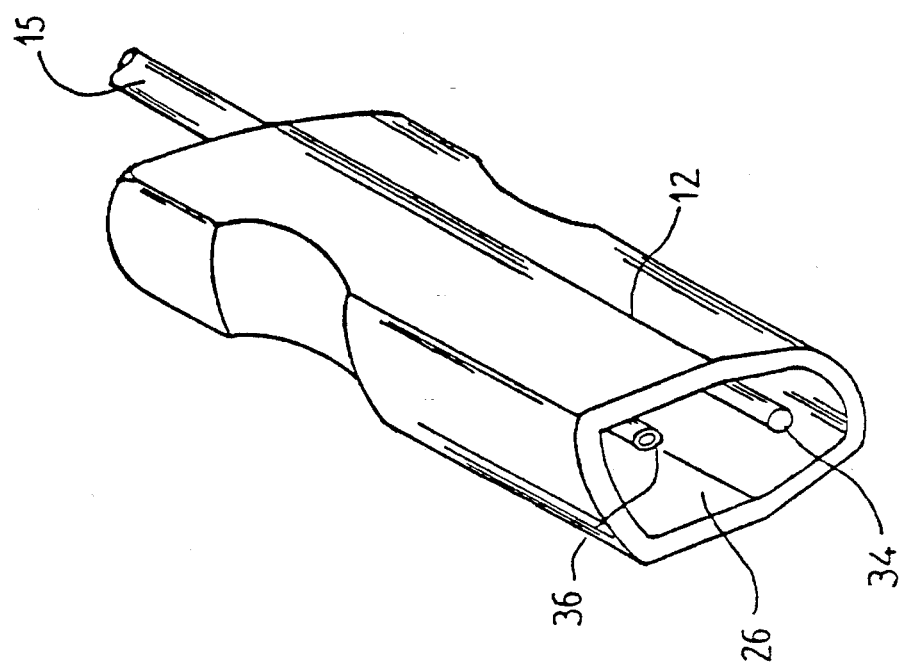
FIG. 4 illustrates a perspective view of the male component of the connector of the present invention.
Figure 2:
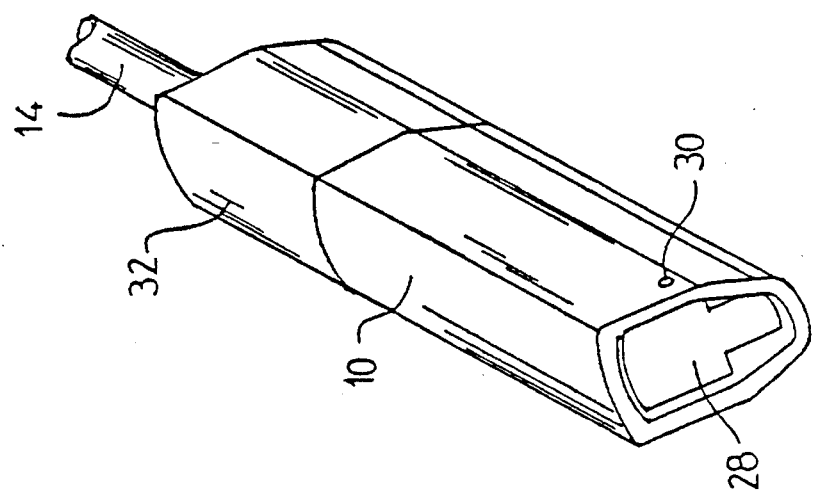
FIG. 2 illustrates a perspective view of the female component of the connector of the present invention with the hinged closure in its sealed position.
Figure 3:
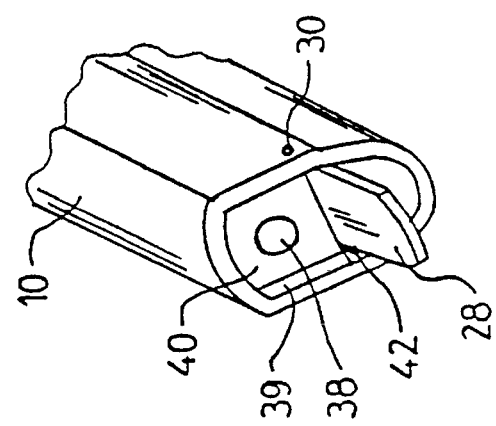
FIG. 3 illustrates a partial perspective view of the female component of the connector of the present invention with the hinged closure in its open position.

Referring now to FIGS. 2, 3 and 4, the female component 10 of the connector 1 is illustrated. The female component 10 has an exterior dimension designed to fit within an opening 26 of the male component 12. The female component includes a hinged door 28 rotatable about a hinge 30. The hinge 30 allows the door 28 to rotate approximately 90° to the position shown in FIG. 3.

As mentioned, the exterior of the female component 10 is designed to fit within the opening of the male component 12 in sliding engagement. Further, the exterior of the female component 10 is designed such that only one orientation of the female component 10 may be received within the opening 26 of the male component 12.

The female component 10 further includes a sleeve 32 capable of axial rotation about the conduit 14. In the position illustrated in FIG. 2, the conduit 14 is pinched closed by a pair of arms within the sleeve 32 which will be described hereinafter with reference to FIGS. 5, 6 and 7.

Referring now to FIG. 4, the male component 12 is illustrated having a longitudinal member 34 extending within the opening 26 and a tubular member 36 extending substantially parallel to the longitudinal member 34 within the opening 26. The longitudinal member 34, during connection of the male component 12 to the female component 10, forces rotation of the door 28 about the hinge 30. The tubular member 36 is guided into the opening 38 (See FIG. 3) of the female component 10 providing fluid communication through the male component 12 and the female component 10.

The door 28 maintains a seal against a surface 40 including the opening 38 via a spring 42. The spring 42 provides tension to maintain the door 28 in the position illustrated in FIG. 2. Insertion of the female component 10 into the male component 12 acts against the tension in the spring 42 of the door 28 causing the door 28 to open allowing the tubular member 36 to be inserted into the opening 38 of the female component 10.

In another embodiment of the present invention, a snap detent may 39 replace the spring 42 or supplement the spring 42 to hold the hinged door 28 in the position shown in FIG. 2. The snap detent 39 is generally known in the art. In the present invention, the snap detent 39 is circumferentially formed as a ridge around the inner circumference of the female component 10. The ridge is formed at a point within the female component 10 where the door 28 is snap fitted in a closed position. Further, the door 28 may be impregnated with an antimicrobial agent to enhance the aseptic procedure during opening and closing of the door 28.

As the female component 10 and the male component 12 are further engaged following opening of the door 28, the tubular member 36 of the male component 12 is sealingly engaged into the opening 38 of the female connector 10. To this end, the opening 38 may be luer tapered to assist in the sealing engagement of the same. In another embodiment, the opening 38 may include an O-ring to maintain the seal therebetween.

Referring now to FIGS. 5 and 6, the connector 1 is shown immediately prior to connection of the female component 10 to the male component 12 (FIG. 5) and after connection therebetween (FIG. 6). The distinction between the connection and disconnection of the female component 10 and the male component 12 is most clearly evident by the position of the door 28.

In the closed position, the door 28 is substantially parallel to an end face of the female component 10 and sealingly covers the opening 38 to which the tubular component 34 connects in fluid communication. The opening 26 or reservoir of the male component 12 separates the tubular member 36 from the longitudinal member 34. When connection of the male component 12 is desired with the female component 10, the male component 12 is slidingly engaged around the female component 12 allowing the longitudinal member 34 to force the door 28 to rotate about the hinge 30.

When the male component 12 is secured over the female component 10 as shown in FIG. 6, the door 28 is perpendicularly disposed with respect to an end face thereof. The opening 26 or reservoir is constructed and arranged to allow a clearance for the door 28 to swing therein as shown in FIG. 6. After connection of the male component 12 to the female component 10, fluid communication between the Y-set 18 and the patient is achieved.

The female component 10 further includes a sleeve 44 partially rotatable about an axis parallel to a length of the conduit 14 between the female component 10 and the patient 2. Within the sleeve 44 are a pair of longitudinal members 46. The sleeve 44 rotates about the axis thereby deflecting the position of the longitudinal members 46 in a conduit compressed position and a flowing position.

To this end, an opening 50 is provided at an end face of the sleeve 44 as shown in FIG. 7. The end face is constructed and arranged such that in one position the end of the longitudinal members 46 are compressed thereby compressing the conduit 14 and, in another rotated position, the longitudinal members 46 are fully expanded into the opening 50 allowing fluid to flow through the conduit 14.

In an embodiment, the opening 50 is rectangular as illustrated in FIG. 7. The conduit 14 is, therefore, compressed as shown with the opening 50 in the position illustrated. When the sleeve 44 is rotated 90°, the opening 50 rotates 90° as well. The leg 46 thereby expands into the length of the rectangular opening 50 allowing fluid to flow through the conduit 14.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A connector assembly comprising:

a male component connected to a first length of tubing; and a female component having a first end and a second end defining an interior wherein the female component is connected to a second length of tubing at the first end and further wherein the female component selectively mates with the male component from the second end providing communication between the first length of tubing and the second length of tubing, the female component having a hinged closure proximate the second end providing selective access to the interior of the female component wherein the hinged closure is rotatable about an axis perpendicular to a length of the female component and extending through the hinged closure.

2. The connector assembly of claim 1 further comprising:

a spring operatively attached to the hinged closure to maintain a seal of the hinged closure.

3. The connector assembly of claim 1 further comprising:

a snap detent forming a ridge around an inner circumferential wall of the female component to maintain a seal of the hinged closure.

4. The connector assembly of claim 1 further comprising:

a longitudinal member within the male component, the longitudinal member capable of opening the hinged closure of the female component.

5. The connector assembly of claim 1 further comprising:

a tubular member within the male component, the tubular member extending such that, when the male component mates with the female component, the orifice of the female component is in fluid communication with the tubular member.

6. The connector assembly of claim 1 further comprising:

an O-ring proximate the second end of the female component at the hinged closure.

7. The connector assembly of claim 1 further comprising:

a luer taper at the second end of the female component at the hinged closure.

8. The connector assembly of claim 1 further comprising:

a clamp at an end of the male component of the female component, the clamp selectively occluding flow through the tubing.

9. The connector assembly of claim 8 wherein the clamp is rotatable about an axis defined along a length of the tubing.

10. A connector assembly for providing fluid communication between a first length of tubing and a second length of tubing, the assembly comprising:

a first component having an interior defined by walls between a first end and a second end wherein the first component includes a hinged closure rotatable about an axis connected to the walls in the interior of the first component and further wherein the first component is connected to the first length of tubing; and a second component having means for opening the hinged closure and connected to the second length of tubing wherein connection of the first component to the second component rotates the hinged closure about the axis and provides fluid communication between the first length of tubing and the second length of tubing.

11. The connector assembly of claim 10 further comprising:

occluder means selectively preventing and permitting flow through one of the lengths of tubing.

12. The connector assembly of claim 11 wherein the occluder means is rotatable about an axis defined by the first length of tubing.

13. The connector assembly of claim 10 further comprising:

a mass integrally formed on an interior side of the hinged closure, the mass sealing an opening of the first component.

14. The connector assembly of claim 13 wherein the mass is antimicrobially impregnated.

15. The connector assembly of claim 10 further comprising:

a spring operatively attached to the hinged closure applying tension to the hinged closure.

16. The connector assembly of claim 10 wherein the first component and the second component are constructed and arranged to prevent misalignment.

17. A method for providing fluid communication between a first length of tubing connected to a patient and a second length of tubing connected to a fluid source, the method comprising the steps of:

providing a first connector having an interior defined by walls between a first end and a second end;

providing a closure attached proximate to the first end of the first connector by an axis perpendicular to a length of the first connector;

providing a second connector;

providing a means for opening the closure integrally formed with the second connector; and connecting the first connector with the second connector providing fluid communication between the first length of tubing and the second length of tubing wherein the means for opening of the second connector forces the closure to rotate about the axis upon connection.

18. The method of claim 17 further comprising the step of:

providing an occluder for selectively preventing fluid communication.

19. The method of claim 17 further comprising the step of:

rotating an occluder about an axis defined by a length of the tubing for selectively preventing fluid communication.

20. The method of claim 17 further comprising the step of:

retaining the closure in a closed position prior to connection of the first connector and the second connector.

* * * * *